United States Patent

Algieri et al.

[11] 4,203,909
[45] May 20, 1980

[54] FURAN COMPOUNDS

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 945,968

[22] Filed: Sep. 26, 1978

[51] Int. Cl.$^2$ .......................................... C07D 307/54
[52] U.S. Cl. ................................. 260/347.2; 424/285
[58] Field of Search ................................... 260/347.2

[56] References Cited

U.S. PATENT DOCUMENTS

| 4,112,234 | 9/1978 | Crenshaw et al. | 548/342 |
| 4,128,658 | 12/1978 | Price et al. | 260/347.2 X |

FOREIGN PATENT DOCUMENTS 841814 11/1976 Belgium.
857388 2/1978 Belgium.

OTHER PUBLICATIONS

Ganellin et al., Federation Proceedings, vol. 35 (1925), pp. 1924–1930.
Drugs of the Future, vol. 1, No. 1 (1976), pp. 13–18.

Primary Examiner—Richard Raymond
Attorney, Agent, or Firm—Richard R. Lloyd

[57] ABSTRACT

Compounds of the formula

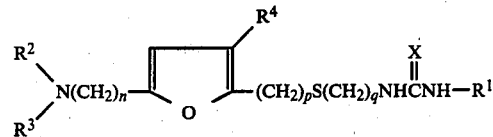

wherein $R^1$ is a straight or branched chain alkynyl group containing from 3 to 9 carbon atoms, inclusive; $R^2$ and $R^3$ are the same or different and are hydrogen, (lower)alkyl, (lower)alkenyl, (lower)alkynyl or Ar; $R^4$ is hydrogen or (lower)alkyl; n is an integer of from 1 to 6; p is 1 or 2 and q is 2 or 3, provided that the sum of p and q is 3 or 4; X is $NR^5$ or $CHR^5$; $R^5$ is cyano, nitro, $SO_2Ar$ or $SO_2$(lower)alkyl; and Ar is an optionally substituted phenyl group; and nontoxic, pharmaceutically acceptable salts thereof, are potent anti-ulcer agents. Processes for their preparation and novel intermediates are also disclosed.

15 Claims, No Drawings

FURAN COMPOUNDS

SUMMARY OF THE INVENTION

This application relates to certain N-alkynyl-N'-{ω-[(5-substituted-2-furyl)alkylthio]alkyl}-derivatives of N''-cyanoguanidine and of 1,1-diamino-2-(substituted)-ethylene which are histamine $H_2$-receptor blocking agents, which inhibit gastric acid secretion and which are useful in the treatment of ulcers; and to processes for, and intermediates in, their preparation.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via $H_2$ receptors and is not inhibited by the classical antihistamines, which are $H_1$-receptor blockers. A number of specific $H_2$-receptor blocking agents ($H_2$-receptor antagonists) are now known. These compounds inhibit basal acid secretion, as well as secretion by other known gastric acid stimulants, and are useful in the treatment of peptic ulcers.

Burimamide (IIa) was the first clinically effective $H_2$-receptor antagonist. It inhibits gastric secretion in animals and man, but oral absorption is poor.

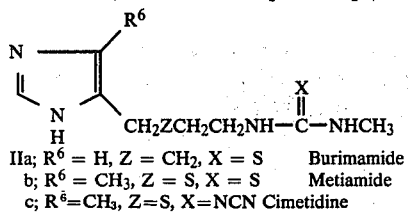

IIa; $R^6$ = H, Z = $CH_2$, X = S  Burimamide
b; $R^6$ = $CH_3$, Z = S, X = S  Metiamide
c; $R^6$=$CH_3$, Z=S, X=NCN  Cimetidine Metiamide (IIb), a subsequently evaluated $H_2$ antagonist, is more potent than burimamide and is orally active in man. Clinical utility was limited, however, owing to toxicity (agranulocytosis). Cimetidine (IIc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200–300 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et al., *Federation Proceedings*, 35, 1924 (1976), in *Drugs of the Future*, 1, 13 (1976), and in references cited therein. Relevant patents are as follows:

Belgian Pat. No. 841,814 (Farmdoc 90568X) discloses inhibitors of histamine-stimulated gastric secretion having the formula

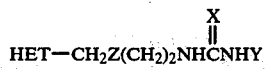

in which HET is one of eight named heterocyclic rings (all of which contain at least one nitrogen, thereby excluding furyl) which may be substituted by (lower)-alkyl, hydroxy, amino or halogen, Z is sulfur or $CH_2$, X is S, $CHNO_2$, NCN or NH, Y is $NH_2$, (lower)alkylamino, di(lower)alkylamino, (lower)alkoxy, phenylethyl, imidazolylethyl, allyl, trifluoroethyl or $(CH_2)_nR$ in which n is 1–12 and R is OH, (lower)alkoxy, $NH_2$ or (lower)-alkylamino; provided that, when X is NH, Y is trifluoroethyl or $(CH_2)_nR$; and when X is NCN, Y may not be amino or alkylamino.

Belgian Pat. No. 857,388 discloses histamine $H_2$-receptor inhibitors of the formula

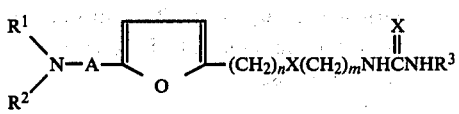

in which $R^1$ and $R^2$ are the same or different and are hydrogen, (lower)alkyl, cycloalkyl, (lower)alkenyl, aralkyl or a (lower)alkyl group which is interrupted by an oxygen atom or by the group $NR^4$ in which $R^4$ is hydrogen or (lower)alkyl, or $R^1$ and $R^2$ together with the nitrogen atom form a heterocyclic ring optionally containing an oxygen atom or an $NR^4$ group; A is (lower)alkylene; m is 2–4; n is 1 or 2, or can be zero when X is sulfur or $CH_2$; X is oxygen, sulfur or $CH_2$; Y is sulfur, oxygen, $NR^5$ or $CHR^6$; $R^5$ is hydrogen, nitro, cyano, (lower)alkyl, aryl, alkylsulfonyl or arylsulfonyl; $R^6$ is nitro, arylsulfonyl or alkylsulfonyl; and $R^3$ is hydrogen, (lower)alkyl, (lower)-alkenyl or alkoxyalkyl.

U.S. Pat. No. 4,112,234 discloses histamine $H_2$-receptor inhibitors of the formula

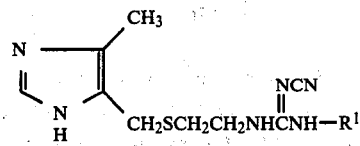

wherein $R^1$ is a straight or branched chain alkynyl group containing from 3 to 9 carbon atoms, inclusive, and processes for the preparation thereof.

COMPLETE DISCLOSURE

This invention relates to histamine $H_2$-receptor antagonists which are effective inhibitors of gastric secretion in animals, including man, which are useful in the treatment of peptic ulcer disease and which have the formula

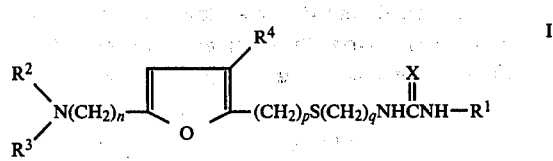

wherein $R^1$ is a straight or branched chain alkynyl group containing from 3 to 9 carbon atoms, inclusive; $R^2$ and $R^3$ are the same or different and are hydrogen, (lower)-alkyl, (lower)alkenyl, (lower)alkynyl or Ar; $R^4$ is hydrogen or (lower)alkyl; n is an integer of from 1 to 6; p is 1 or 2 and g is 2 or 3, provided that the sum of p and q is 3 or 4; X is $NR^5$ or $CHR^5$; $R^5$ is cyano, nitro, $SO_2Ar$ or $SO_2$-(lower)alkyl; and Ar is an optionally substituted phenyl group; and nontoxic, pharmaceutically acceptable salts thereof.

A preferred embodiment of the invention is a compound of the formula

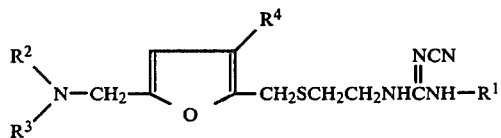
Ia wherein $R^1$, $R^2$, $R^3$ and $R^4$ are as described above, or a nontoxic, pharmaceutically acceptable salt thereof.

Another preferred embodiment of the invention is a compound of the formula

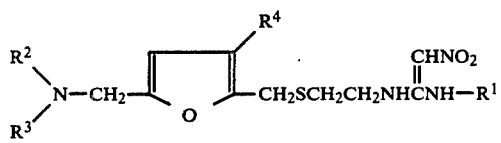
Ib wherein $R^1$, $R^2$, $R^3$ and $R^4$ are as described above, or a nontoxic, pharmaceutically acceptable salt thereof.

A more preferred embodiment of the invention is a compound of the formula

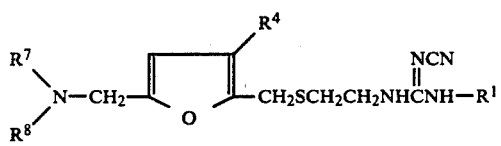
Ic wherein $R^1$ and $R^4$ are as described above and $R^7$ and $R^8$ are the same or different and are hydrogen or (lower)alkyl, or a nontoxic, pharmaceutically acceptable salt thereof.

Another more preferred embodiment of the invention is a compound of the formula

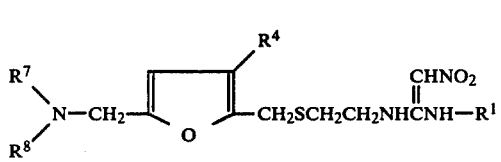
Id wherein $R^1$, $R^4$, $R^7$ and $R^8$ are as described above, or a nontoxic, pharmaceutically acceptable salt thereof.

A still more preferred embodiment of the invention is a compound of the formula

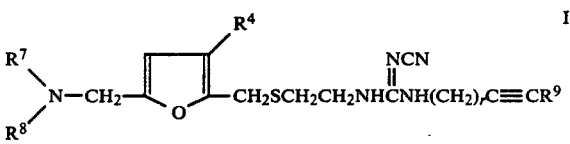
Ie wherein $R^4$, $R^7$ and $R^8$ are as described above, r is an integer of from 1 to 6, inclusive, and $R^9$ is hydrogen or methyl, or a nontoxic, pharmaceutically acceptable salt thereof.

Another still more preferred embodiment of the invention is a compound of the formula

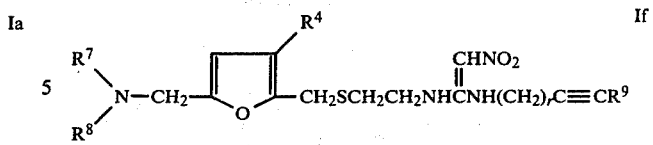
If wherein $R^4$, $R^7$, $R^8$, $R^9$ and r are as described above, or a nontoxic, pharmaceutically acceptable salt thereof.

Another still more preferred embodiment of the invention is a compound of the formula

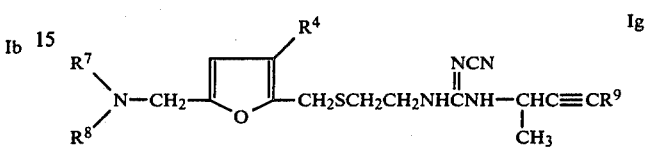
Ig wherein $R^4$, $R^7$, $R^8$ and $R^9$ are as described above, or a nontoxic, pharmaceutically acceptable salt thereof.

Another still more preferred embodiment of the invention is a compound of the formula

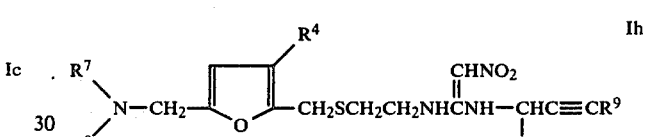
Ih wherein $R^4$, $R^7$, $R^8$ and $R^9$ are as described above, or a nontoxic, pharmaceutically acceptable salt thereof.

Another still more preferred embodiment of the invention is a compound of the formula

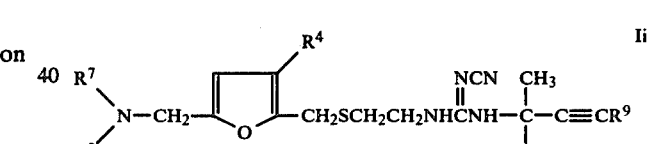
Ii wherein $R^4$, $R^7$, $R^8$ and $R^9$ are as described above, or a nontoxic, pharmaceutically acceptable salt thereof.

Another still more preferred embodiment of the invention is a compound of the formula

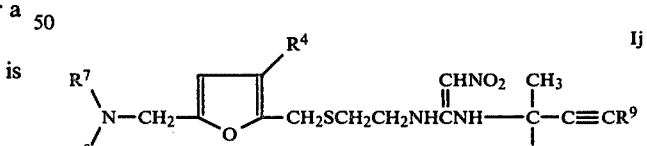
Ij wherein $R^4$, $R^7$, $R^8$ and $R^9$ are as described above, or a nontoxic, pharmaceutically acceptable salt thereof.

A most preferred embodiment is a compound of the formula

Ik or a nontoxic pharmaceutically acceptable salt thereof.

Another most preferred embodiment of the invention is the compound of the formula

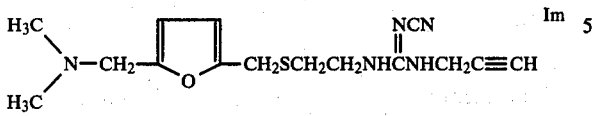

or a nontoxic, pharmaceutically acceptable salt thereof.

Although the compounds of this invention have been shown as having the structure of Formula I, it will be appreciated by those skilled in the art that the compounds in which X is $CHR^5$ can exist in various tautomeric forms, as follows:

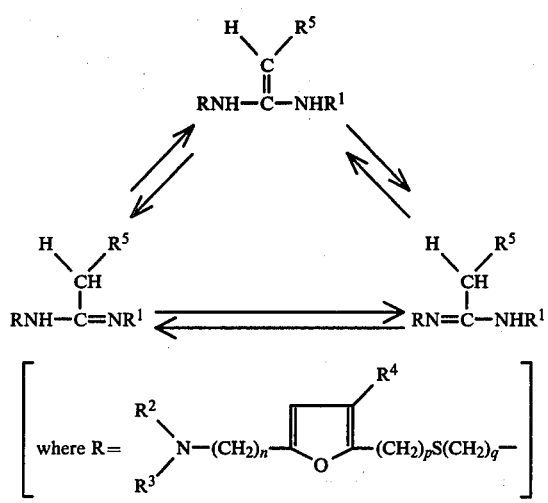

Also, the compounds in which X is $CHR^5$ may exist as two geometric isomers, i.e., cis/trans isomers about the double bond. In addition, all the compounds of Formula I which contain a branched chain alkynyl group as substituent $R^1$ may exist as their d- or l- optical isomers as well as their racemic forms. Thus, for example 3-amino-1-butyne of the formula

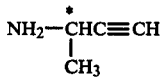

may be resolved into its d- and l- isomers as described by A. Marszak-Fleury, *Compt. rend.*, 242, 1046 (1956). The use of the d- or l- isomer of the alkynylamine in the preparation of a compound of Formula I produces the corresponding d- or l- isomer of the compound of Formula I. The present invention includes within its scope all possible tautomeric forms, geometric isomers and optical isomers of the compounds of Formula I as well as mixtures thereof.

The compounds of the present invention may be prepared by various alternative reaction schemes, as illustrated below for preferred compounds Ik and Im.

Scheme I

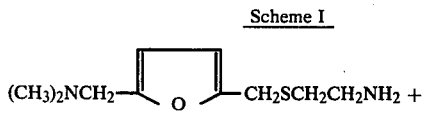

-continued
Scheme I

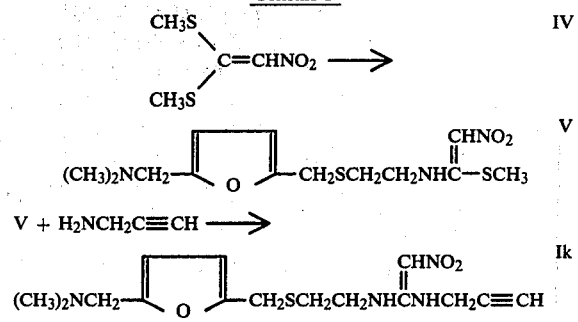

The compound of Formula III is prepared by the procedure described in Belgian Pat. No. 857,388. Analogous and homologous compounds are prepared by procedures described in Belgian Patent 857,388 or by analogous procedures. The compound of Formula IV is prepared by procedures described in *Chem. Ber.*, 100, 591 (1967) and *Acta. Chem. Scand.*, 21, 2797 (1967). The reaction steps of Scheme I are conducted in a non-reactive solvent at or above room temperature. The alkynylamines utilized as starting materials (propargylamine illustrated above) are either commercially available or may be prepared by procedures described in *Bull. Soc. Chim. Fi.*, 490 (1958), *Bull. Soc. Chim. Fr.*, 588 (1967), *Bull. Soc. Chim. Fr.*, 592 (1967), *Annales de Chimie* (Paris), 3, 656 (1958) and *J. Org. Chem.*, 21, 791 (1956).

Scheme II

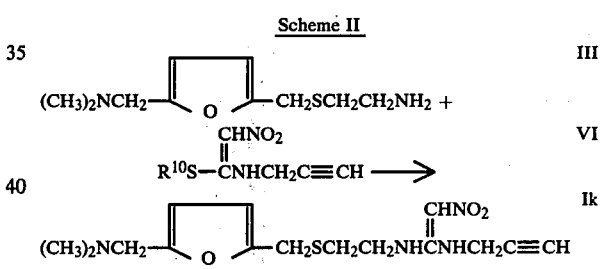

The reaction is conducted in a non-reactive solvent at or above room temperature. As will be appreciated by those skilled in the art, $R^{10}$ may be any substituent such that $-SR^{10}$ will be a suitable leaving group. Such leaving groups are conventional in the art. Thus, $R^{10}$ may be (lower)alkyl, aryl or substituted aryl (e.g. p-nitrophenyl), or the like. The compounds of Formula VI may themselves be prepared by alternative procedures, such as illustrated below for the preparation of Compound VI wherein $R^{10}$ is methyl.

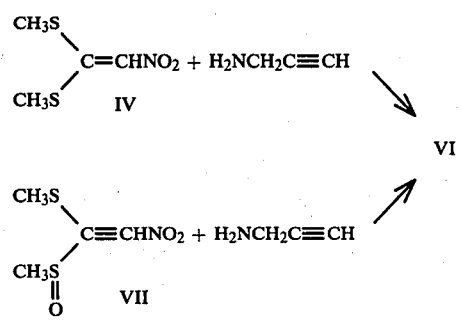

The compound of Formula VII is prepared by the procedures described in Belgian Pat. No. 841,526 and analogous compounds may be prepared by analogous procedures. It will be apparent to those skilled in the art that, if the propargylamine utilized above is replaced by a different alkynylamine, there will be produced a compound of Formula VI which contains the different alkynyl group. That compound, in turn, can be reacted with a compound of Formula III to produce a compound of Formula I containing the different alkynyl group.

Scheme III

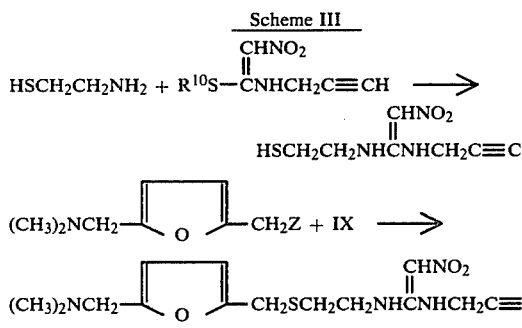

The reaction steps are conducted in a non-reactive solvent at or above room temperature. Compound VI is prepared as described above in Scheme II. Substituent Z in Compound X is a conventional leaving group. Suitable leaving groups "Z" for use in this reaction are well-known to those skilled in the art. They include, for example, fluoro, chloro, bromo, iodo, —O$_3$SR$^{11}$ wherein R$^{11}$ is (lower)alkyl [e.g. methanesulfonate], —O$_3$SR$^{12}$ wherein R$^{12}$ is aryl or substituted aryl [e.g. benzenesulfonate, p-bromobenzenesulfonate or p-toluenesulfonate], —O$_3$SF, acetoxy and 2,4-dinitrophenoxy. For convenience and economy we normally prefer to utilize compound X in which Z is chloro. The compound of Formula X, and analogous compounds, may be prepared by procedures described in Belgian Pat. No. 857,388.

Scheme IV

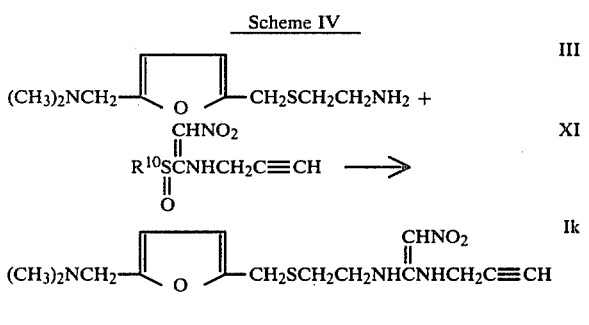

The reaction is conducted in a non-reactive solvent at or above room temperature. The compound of Formula XI, in which R$^{10}$ is as described above, is prepared by oxidation of a compound of Formula VI by conventional means.

Scheme V

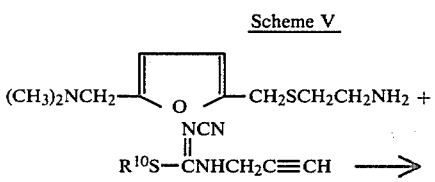

-continued
Scheme V

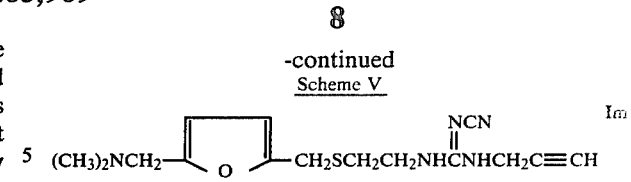

The reaction is conducted in a non-reactive solvent at or above room temperature. The compounds of Formula XII may be prepared by procedures described in our colleagues U.S. patent application Ser. No. 936,668, filed Aug. 24, 1978, the complete disclosure of which is incorporated herein by reference. For example, Compound XII in which R$^{10}$ is methyl may be prepared by reacting dimethyl cyanodithioimidocarbonate with propargylamine. The dimethyl cyanodithioimidocarbonate may itself be prepared by procedures described in *J. Org. Chem.*, 32, 1566 (1967). Analogous compounds may be prepared by analogous procedures.

Scheme VI

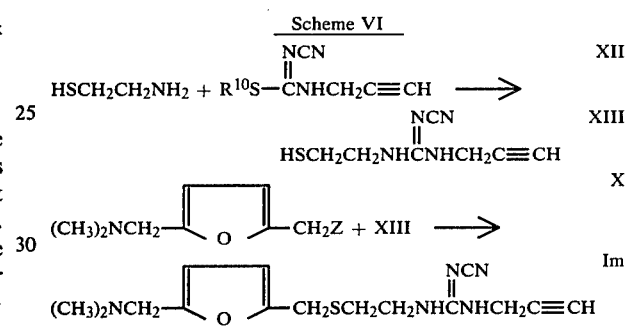

The reaction, which is analogous to that described in Scheme III above, is conducted in a non-reactive solvent at or above room temperature. The compound of Formula XII and homologous and analogous compounds containing other alkynyl groups are described and claimed in our colleagues U.S. patent application Ser. No. 906,901, filed May 18, 1978, the complete disclosure of which is incorporated herein by reference.

Scheme VII

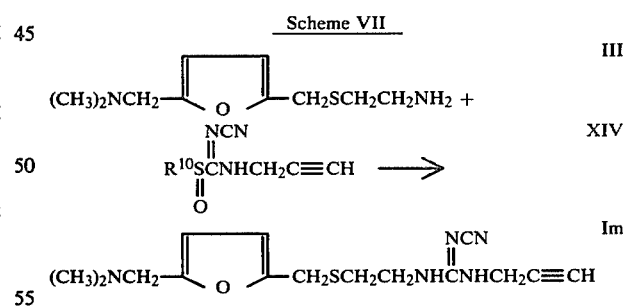

The reaction, which is analogous to that described in Scheme IV above, is conducted in a non-reactive solvent at or above room temperature. The compounds of Formula XIV are prepared by oxidation of a compound of Formula XII by conventional means.

Scheme VIII

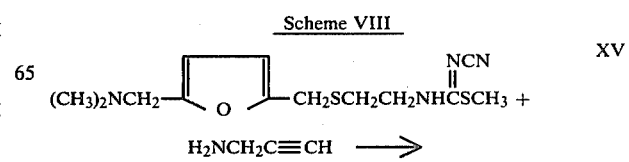

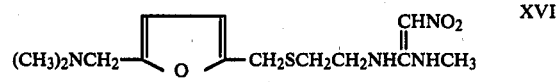

-continued

The reaction, which is analogous to that described in the second step of Scheme I above, is conducted in a non-reactive solvent at or above room temperature. The compound of formula XV is prepared by the procedure described in Belgian Pat. No. 857,388.

As used herein, the term nontoxic pharmaceutically acceptable acid addition salt means the mono- or di-salt of a compound of this invention with a nontoxic pharmaceutically acceptable organic or inorganic acid. Such acids are well known and include hydrochloric, hydrobromic, sulfuric, sulfamic, phosphoric, nitric, maleic, fumaric succinic, oxalic, benzoic, methanesulfonic, ethanedisulfonic, benzenesulfonic, acetic, propionic, tartaric, citric, camphorsulfonic, and the like. The salts are made by methods known in the art.

Substituent Ar is defined above as optionally substituted phenyl. As used herein it is intended that Ar include unsubstituted phenyl and phenyl containing 1 or 2 substituents independently selected from (lower)alkyl and halogen. The term "(lower)alkyl", as used herein, means a straight or branched chain alkyl group containing from 1 to 6 carbon atoms.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or nonaqueous liquid suspension. The pharmaceutical compositions are prepared by conventional techniques appropriate to the desired preparation.

Preferably, each dosage unit will contain the active ingredient in an amount of from about 10 mg. to about 250 mg., and most preferably from about 20 mg. to about 200 mg. The active ingredient will preferably be administered in equal doses from two to four times a day. The daily dosage regimen will preferably be from 50 mg. to about 1000 mg., and most preferably from about 100 mg. to about 750 mg.

Histamine $H_2$-receptor antagonists have been shown to be effective inhibitors of gastric secretion in animals and man, Brimblecombe et al., J. Int. Med. Res., 3, 86 (1975). Clinical evaluation of the histamine $H_2$-receptor antagonist cimetidine has shown it to be an effective therapeutic agent in the treatment of peptic ulcer disease, Gray et al., Lancet, 1 (8001), 4 (1977). The compounds prepared in Examples 1 and 2 below (hereinafter referred to as BL-5966 and BL-5993 have been compared, in various tests, with cimetidine and the structurally related compound of Formula XVI (disclosed in Belgian Pat. No. 857,388). BL-5966 has been shown to be more potent than either cimetidine or Compound XVI both as a histamine $H_2$ receptor antagonist in isolated guinea pig atria and as an inhibitor of gastric secretion in rats and dogs.

Histamine $H_2$-Receptor Antagonism-Isolated Guinea Pig Atria Assay

Histamine produces concentration-related increases in the contractile rate of isolated, spontaneously beating guinea pig right atria. Black et al., Nature, 236, 385 (1972), described the receptors involved in this effect of histamine as histamine $H_2$-receptors when they reported the properties of burimamide, a competitive antagonist of these receptors. Subsequent investigations by Hughes and Coret, Proc. Soc. Exp. Biol. Med., 148, 127 (1975) and Verma and McNeill, J. Pharmacol. Exp. Ther., 200, 352 (1977) support the conclusion of Black and coworkers that the positive chronotropic effect of histamine in isolated guinea pig right atria is mediated via histamine $H_2$-receptors. Black et al., Agents and Actions, 3, 133 (1973) and Brimblecombe et al., Fed. Proc., 35, 1931 (1976) have utilized isolated guinea pig right atria as a means for comparing the activities of histamine $H_2$-receptor antagonists. The present comparative studies were carried out using a modification of the procedure reported by Reinhardt et al., Agents and Actions, 4, 217 (1974).

Male Hartley strain guinea pigs (350–450 gm.) were sacrificed by a blow on the head. The heart was excised and placed in a Petri dish of oxygenated (95% $O_2$, 5% $CO_2$) modified Krebs solution (g./liter: NaCl 6.6, KCl 0.35, $MgSO_4.7 H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-0) attached to each end. The atrium was suspended in a 20 ml. muscle chamber containing oxygenated modified Krebs solution maintained at 32° C. Atrial contractions were recorded isometrically by means of a Grass FT 0.03 force displacement transducer and recordings of contractile force and rate were made with a Beckman RP Dynograph.

A resting tension of 1 g. was applied to the atrium and it was allowed to equilibrate for 1 hour. At the end of the equilibration period a submaximal concentration of histamine dihydrochloride ($3 \times 10^{-6}$ M) was added to the bath and washed out to prime the tissue. Histamine was then added to the bath in a cumulative fashion using ½ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$ M concentration. The histamine was washed out several times and the atrium allowed to return to control rate. The test compound ($3 \times 10^{-5}$ M) was then added and after a 30 minute incubation the histamine concentration-response was repeated adding higher concentrations as needed.

The histamine ED50 values (concentration of histamine which increased contractile rate 50% of maximum) and 95% confidence limits before and after the test compound were obtained by regression analysis as described by Finney, *Probit Analysis*, 3rd ed., Cambridge (1971). Concentration-response curve displacement factors were calculated as follows:

$$\text{Displacement factor} = \frac{\text{ED50 Histamine + Compound}}{\text{ED50 Histamine Alone}}$$

The factors obtained for BL-5966, BL-5993 and Compound XVI were then expressed as ratios of the factor obtained for cimetidine.

$$\text{Activity Ratio} = \frac{\text{Test Compound Displacement Factor} - 1}{\text{Cimetidine Displacement Factor} - 1}$$

The results obtained from these studies are summarized in Table 1. Cimetidine and Compound XVI displaced the histamine concentration-response curve to the right by factors of 25.26 and 38.61, respectively, while BL-5966 and BL-5993 displaced the curve to the right by factors of 181.67 and 23.78, respectively. Based on the concentration-response curve displacement of factors, Compound XVI was about 1.55 times more active than cimetidine, BL-5966 was about 7.45 times more active than cimetidine and BL-5933 was about 0.94 times as active as cimetidine as histamine $H_2$-receptor antagonists in isolated guinea pig right atria. BL-5966 was about 4.80 times more active than Compound XVI in this model.

After wound closure, ether administration is stopped and either BL-5966, BL-5993, Compound XVI, cimetidine or vehicle is administered intraperitoneally in a volume of 1 mg./kg. All compounds are solubilized with one equivalent of HCl and brought to the proper volume with water. The animals are returned to their cages from which the water bottles have been removed and two hours later are sacrificed with ether. The stomach is removed and the two hour gastric collection is drained into a graduated test tube for volume determination. Titratable acidity is measured by titrating a one ml. sample to pH 7.0 with 0.02 N NaOH, using an Autoburet and an electrometric pH meter (Radiometer). Titratable acid output is calculated in microequivalents by multiplying the volume in milliliters by the acid concentration in milliequivalents per liter. The percent inhibition of acid output is calculated as follows % Inhibition Acid Output =
$$\frac{\text{Acid Output-Control} - \text{Acid Output-Drug}}{\text{Acid Output-Control}} \times 100$$

The test results are summarized in Table 2. These results indicate that, in the two hour pylorus ligated rat preparation, BL-5966 is 5.81, BL-5993 is 0.83 and Compound XVI is 2.31 times as potent as cimetidine. It is also evident that BL-5966 is 2.52 times more potent than Compound XVI.

Table 1

Relative Activity of Cimetidine, Compound XVI, BL-5966 and BL-5993 in Isolated Guinea Pig Right Atria

| Compound | N | Concentration | Histamine ED50 With 95% Confidence Limits (μg/ml) | Concentration-Response Curve Displacement Factor | Activity Ratio Relative to Cimetidine |
|---|---|---|---|---|---|
| Histamine control | 8 | — | 0.19 (0.15–0.24) | — | — |
| Cimetidine | 8 | $3 \times 10^{-5}$M | 4.80 (3.9–5.9) | 25.26 | 1.0 |
| Histamine control | 2 | — | 0.31 (0.21–0.46) | — | — |
| Compound XVI | 2 | $3 \times 10^{-5}$M | 11.97 (5.00–29.20) | 38.61 | 1.55 |
| Histamine control | 2 | — | 0.18 (0.15–0.22) | — | — |
| BL-5966 | 2 | $3 \times 10^{-5}$M | 32.70 (20.10–63.93) | 181.67 | 7.45 |
| Histamine control | 2 | — | 0.18 (0.14–0.23) | — | — |
| BL-5993 | 2 | $3 \times 10^{-5}$M | 4.28 (2.70–7.00) | 23.78 | 0.94 |

N = number of experiments

Determination of Gastric Antisecretory Activity in the Two Hour Pylorus Ligated (Shay) Rat The pyloric ligation procedure in the rat was designed by Shay et al., *Gastroenterology*, 5, 53 (1945) for the study of perforating gastric ulcers; however, as the method became known, it was also employed as a means of studying rat gastric secretion, Shay et al., *Gastroenterology*, 26, 906 (1954), Brodie, D. A., *Am. J. Dig. Dis.*, 11, 231 (1966). A modification of this procedure is presently used to evaluate compounds for gastric antisecretory activity.

Male Long Evans rats, 280–300 gm., are used. The aimals are placed in individual cages and fasted for 24 hours with free access to water. Under ther anesthesia, the stomach is reached through a midline incision, and a cotton-thread ligature is placed around the pylorus.

Table 2

Effect of BL-5966, BL-5993, Compound XVI and Cimetidine on Gastric Acid Output in the Two Hour Pylorus Ligated Rat

| Compound | Dose (ip)[a] μMole/kg | Percent Inhibition Acid Output | ED50 μMole/kg | Potency Ratio |
|---|---|---|---|---|
| BL-5966 | 5 | 83 | | |
|  | 2.5 | 59 | 1.80 | 5.81 |
|  | 1.25 | 36 | | |
|  | 0.625 | 27 | | |
| BL-5993 | 20 | 71 | | |
|  |  |  | 12.5 | 0.83 |
|  | 10 | 34 | | |
| Compound XVI | 20 | 89 | | |
|  | 10 | 77 | 4.52 | 2.31 |
|  | 5 | 42 | | |
| Cimetidine | 40 | 72 | | |
|  | 20 | 57 | | |
|  | 10 | 41 | 10.4 | 1.00 |

Table 2-continued

Effect of BL-5966, BL-5993, Compound XVI and Cimetidine on Gastric Acid Output in the Two Hour Pylorus Ligated Rat

| Compound | Dose (ip)[a] μMole/kg | Percent Inhibition Acid Output | ED50 μMole/kg | Potency Ratio |
|---|---|---|---|---|
|  | 5 | 53 |  |  |
|  | 2.5 | 9 |  |  |

[a] At lease 5 animals were employed at each dose.

Determination of Gastric Antisecretory Activity in the Gastric Fistula Dog

Thomas type [Thomas, J. E., *Proc. Soc. Exp. Biol. Med.*, 46, 260 (1971)] stainless steel cannulae are inserted into the stomachs of beagle dogs (10–12 kg.) just orad to the pyloric gland area near the greater curvature to provide a chronic gastric fistula. Animals are allowed to recover for at least two months before any testing is done. Dogs are fasted overnight (~18 hours) with water ad lib prior to each experiment. The dogs are placed in a sling and an eight inch inside needle catheter (C. R. Baird, Inc.) with a two inch 17 gauge needle is inserted into a leg vein for purposes of drug administration. Gastric secretions are collected every 15 minutes by gravity drainage from the opened cannula. Basal secretions are collected for two consecutive 15 minute periods and if these prove to be excessive (>4 ml./15 min.; pH <5.0) the animal is not used. A modification of the procedure described by Grossman and Konturek, *Gastroenterology*, 66, 517 (1974) was followed. Immediately after the second basal collection, histamine (100 μg./kg./hr.) is infused for 90 minutes with a Harvard Infusion Pump in a volume of 6 ml./hr. At this time either BL-5966, cimetidine (solubilized with one equivalent of HCl and brought a proper volume with normal saline) or normal saline is injected rapidly (within 30 seconds) in a volume of 0.1 ml./kg. and then infusion of histamine continues for an additional 60 minutes (total time of infusion is 2.5 hours). Each 15 minute sample of gastric juice is measured to the nearest 0.5 ml. and titratable acidity against 0.02 N NaOH (endpoint pH 7.0) is measured with an Autoburet and pH meter (radiometer). The percent inhibition of acid output is calculated as described in the pylorus ligated rat procedure.

The results of the tests are summarized in Table 3. It is evident that BL-5966 is 11.5 times more potent than cimetidine with respect to the inhibition of gastric acid output in gastric fistula dogs.

Table 3

Effect of BL-5966 and Cimetidine on Gastric Acid Output in the Gastric Fistula Dog

| Compound | Dose (iv) μMole/kg | N | Percent Inhibition Acid Output | ED50 μMole/kg | Potency Ratio |
|---|---|---|---|---|---|
| BL-5996 | 0.375 | 2 | 90 |  |  |
|  | 0.1875 | 3 | 46 | 0.12 | 11.5 |
|  | 0.0938 | 3 | 47 |  |  |
|  | 0.0469 | 3 | 32 |  |  |
| Cimetidine | 3.0 | 8 | 73 |  |  |
|  | 1.5 | 11 | 53 | 1.32 | 1.0 |
|  | 0.75 | 3 | 37 |  |  |

N = number of dogs employed at each dose.

EXAMPLE 1

1-Nitro-2-(2-propynylamino)-2-{2-[(5-dimethylaminomethyl-2-furyl)methylthio]ethylamino}ethylene (BL-5966)

A.

1-Nitro-2-methylthio-2-{2-[(5-dimethylaminomethyl-2-furyl)methylthio]ethylamino}ethylene A mixture of 2-[(5-dimethylaminomethyl-2-furyl)methylthio]ethylamine (12.86 g, 60 mmole) [prepared by the procedure described in Belgian Pat. No. 857,388] and 1,1-bis(methylthio)-2-nitroethylene (9.91 g, 60 mmole) [prepared according to the procedure described in *Chem. Ber.*, 100, 591 (1967) and *Acta Chem. Scand.*, 21. 2797 (1967)] in acetonitrile (150 ml) was stirred and heated to reflux temperature under a positive pressure of nitrogen for 15.5 hours. The solvent was removed by evaporation under reduced pressure and the crude product placed on silica gel and chromatographed using a gradient elution of methylene chloride-methanol. The appropriate fractions were combined to yield the title compound (12.6 g).

B.

1-Nitro-2-(2-propynylamino)-2-{2-[(5-dimethylaminomethyl-2-furyl)methylthio]ethylamino≡ethylene (BL-5966)

A mixture of the product of Step A (3.04 g, 9.17 mmole) and distilled propargylamine (6 ml) in acetonitrile (30 ml) was stirred and heated to reflux temperature under a positive pressure of nitrogen for 19 hours. The reaction mixture was evaporated under a reduced pressure and the residue placed on silica gel and chromatographed using a gradient elution of methylene chloridemethanol. The appropriate fractions were combined and evaporated. The residue was dissolved in warm acetonitrile, treated with charcoal then diluted with diethyl ether to give the title compound, mp 125°–127°.

Anal. Calcd for $C_{15}H_{22}N_4O_3S$: C, 53.23; H, 6.55; N, 16.56; S, 9.48. Found: C, 53.25; H, 6.53; N, 16.95; S, 9.67.

EXAMPLE 2

1-Nitro-2-(2-propynylamino)-2-{2-[(5-dimethylaminomethyl-2-furyl)methylthio]ethylamino}ethylene (BL-5966)

A. 1-Methylthio-1-(2-propynylamino)-2-nitroethylene

A solution of propargylamine (1.10 g, 0.02 mole) in 22 ml of methanol was added dropwise to a stirred suspension of 1-methylsulfinyl-1-methylthio-2-nitroethylene [prepared according to the procedure described in Belgian Pat. No. 841,526] at 25°. After 1 hour at ambient temperature, the solution was evaporated under reduced pressure, triturated under 20 ml of cold isopropyl alcohol and filtered to give the product. Recrystallization from isopropyl alcohol gave the title compound, mp 131°–132°.

B.

1-Nitro-2-(2-propynylamino)-2-{2-[(5-dimethylaminomethyl-2-furyl)methylthio]ethylamino}ethylene (BL-5966)

A solution of the product of Step A is reacted with about an equimolar amount of 2-[(5-dimethylaminomethyl-2-furyl)methylthio]ethylamine to give, after workup and chromatography as in Example 1, the title compound.

The product prepared in Step A may alternatively be prepared by reacting about equimolar amounts of 1,1-bis(methylthio)-2-nitroethylene and propargylamine in a non-reactive solvent.

EXAMPLE 3

N-Cyano-N'-(2-propyn-1-yl)-N"-{2-[(5-dimethylaminomethyl-2-furyl)methylthio]ethyl}guanidine (BL-5993)

A mixture of N-cyano-N'-{2-[(5-dimethylaminomethyl-2-furyl)methylthio]ethyl}-S-methylisothiourea (4.0 g, 12.8 mmole) [prepared according to the procedure described in Belgian Patent No. 857,388] and distilled propargylamine (4.0 ml) in methanol (20 ml) was stirred at reflux temperature under a positive pressure of nitrogen for 19 hours. The reaction mixture was evaporated under reduced pressure and the residual oil placed on silica gel and chromatographed using a gradient elution with methylene chloride-methanol. The appropriate fractions were combined to give product (2.04 g). Recrystallization from acetonitrile with charcoal treatment gave the title compound, mp 122°–124°.

Anal. Calcd for $C_{15}H_{21}N_5OS$: C, 56.40; H, 6.63; N, 21.93; S, 10.04. Found: C, 56.35; H, 6.72; N, 22.07; S, 10.10.

EXAMPLE 4

N-Cyano-N'-(2-propyn-1-yl)-N"-{2-[(5-dimethylaminomethyl-2-furyl)methylthio]ethyl}guanidine (BL-5993)

A. N-Cyano-N'-(2-propyn-1-yl)-S-methylisothiourea

A solution of dimethyl cyanodithioimidocarbonate [prepared according to the procedure described in *J. Org. Chem.*, 32, 1566 (1967)] (16.0 g, 0.109 mole) and propargylamine (6.03 g, 0.109 mole) in acetonitrile (320 ml) was stirred at releux for 4 hours, then at 25° for 12 hours. Workup gave the title compound (13.58 g, 81%), mp 160°–164°.

B. N-Cyano-N'-(2-propyn-1-yl)-N"-{2-[(5-dimethylaminomethyl-2-furyl)methylthio]ethyl}guanidine (BL-5993)

The product of Step A is reacted with about an equimolar amount of 2-[(5-dimethylaminomethyl-2-furyl)methylthio]ethylamine in a non-reactive solvent to give, after workup and chromatography as in Example 3, the title product.

EXAMPLE 5

1-Nitro-2-(2-propynylamino)-2-{2-[(5-methylaminomethyl-2-furyl)methylthio]ethylamino}ethylene A mixture of 1-nitro-2-methylthio-2-{2-[(5-methylaminomethyl-2-furyl)methylthio]ethylamino}ethylene [prepared according to the procedure described in Belgian Pat. No. 857,388] and propargylamine in acetonitrile is stirred and heated under a positive pressure of nitrogen to give, after workup and chromatography, the title compound.

EXAMPLE 6

N-Cyano-N'-(2-propyn-1-yl)-N"-{2-[(5-methylaminomethyl-2-furyl)methylthio]ethyl}guanidine A mixture of N-cyano-N'-{2-[(5-methylaminomethyl-2-furyl)methylthio]ethyl}-S-methylisothiourea [prepared according to the procedure described in Belgian Pat. No. 857,388] and propargylamine in methanol is stirred and heated under a positive pressure of nitrogen to give, after workup and chromatography, the title compound.

EXAMPLE 7

The general procedure of Example 1 is repeated except that the propargylamine utilized therein is replaced by an equimolar amount of 2-butyn-1-amine,
3-butyn-1-amine,
4-pentyn-1-amine,
3-amino-1-butyne and
1,1-dimethylpropargylamine, respectively,
and there is thereby produced 1-nitro-2-(2-butyn-1-ylamino)-2-{2-[(5-dimethylaminomethyl-2-furyl)methylthio]ethylamino}ethylene,
1-nitro-2-(3-butyn-1-ylamino)-2-{2-[(5-dimethylaminomethyl-2-furyl)methylthio]ethylamino}ethylene,
1-nitro-2-(4-pentyn-1-ylamino)-2-{2-[(5-dimethylaminomethyl-2-furyl)methylthio]ethylamino}ethylene,
1-nitro-2-(3-butyn-2-ylamino)-2-{2-[(5-dimethylaminomethyl-2-furyl)methylthio]ethylamino}ethylene and
1-nitro-2-(2-methyl-3-butyn-2-ylamino)-2-{2-[(5-dimethylaminomethyl-2-furyl)methylthio]ethylamino}ethylene, respectively.

EXAMPLE 8

The general procedure of Example 3 is repeated except that the propargylamine utilized therein is replaced by an equimolar amount of 2-butyn-1-amine,
3-butyn-1-amine,
4-pentyn-1-amine,
3-amino-1-butyne and
1,1-dimethylpropargylamine, respectively,
and there is thereby produced
N-cyano-N'-(2-butyn-1-yl)-N"-{2-[(5-dimethylaminomethyl-2-furyl)methylthio]ethyl}guanidine,
N-cyano-N'-(3-butyn-1-yl)-N"-{2-[(5-dimethylaminomethyl-2-furyl)methylthio]ethyl}guanidine,
N-cyano-N'-(4-pentyn-1-yl)-N"-{2-[(5-dimethylaminomethyl-2-furyl)methylthio]ethyl}guanidine,
N-cyano-N'-(3-butyn-2-yl)-N"-{2-[(5-dimethylaminomethyl-2-furyl)methylthio]ethyl}guanidine and
N-cyano-N'-(2-methyl-3-butyn-2-yl)-N"-{2-[(5-dimethylaminomethyl-2-furyl)methylthio]ethyl}guanidine, respectively.

EXAMPLE 9

N-Cyano-N'-(2-butyn-1-yl)-N''-{2-[(5-dimethylaminomethyl-2-furyl)methylthio]ethyl}guanidine 2-[(5-Dimethylaminomethyl-2-furyl)methylthio]ethylamine is reacted in a non-reactive solvent with about an equimolar amount of N-(2-butyn-1-yl)-N'-cyano-S-methylisothiourea [prepared according to the procedure described in U.S. Pat. No. 4,112,234, the complete disclosure of which is incorporated herein by reference] and, after workup and chromatography, the title product is produced.

EXAMPLE 10

A solution of propargylamine in methanol is added dropwise to a stirred methanol suspension of an approximately equimolar amount of 1,1-bis(methylthio)-2-nitroethylene,
1,1-bis(ethylthio)-2-nitroethylene,
1,1-bis(benzylthio)-2-nitroethylene and
1,1-bis(2,4-dinitrophenylthio)-2-nitroethylene, respectively, and there is thereby produced
1-methylthio-1-(2-propynylamino)-2-nitroethylene,
1-ethylthio-1-(2-propynylamino)-2-nitroethylene,
1-benzylthio-1-(2-propynylamino)-2-nitroethylene and
1-(2,4-dinitrophenylthio)-1-(2-propynylamino)-2-nitroethylene, respectively.

Reaction of each of the above products with 2-[(5-dimethylaminomethyl-2-furyl)methylthio]ethylamine produces in each case 1-nitro-2-(2-propynylamino)-2-{2-[(5-dimethylaminomethyl-2-furyl)methylthio]ethylamino}ethylene (BL-5966).

The 1,1-bis(methylthio)-2-nitroethylene, 1,1-bis(ethylthio)-2-nitroethylene and 1,1-bis(benzylthio)-2-nitroethylene starting materials are prepared by procedures described in *Chem. Ber.*, 100, 591 (1967) and *Acta Chem. Scand.*, 21, 2797 (1967). The 1,1-bis(2,4-dinitrophenylthio)-2-nitroethylene starting material is prepared by the reaction of 2,4-dinitrofluorobenzene and dipotassium nitrodithioacetate.

EXAMPLE 11

A solution of cysteamine hydrochloride in dimethylformamide is reacted with about an equimolar amount of 1-methylthio-1-(2-propynylamino)-2-nitroethylene,
1-ethylthio-1-(2-propynylamino)-2-nitroethylene,
1-benzylthio-1-(2-propynylamino)-2-nitroethylene and
1-(2,4-dinitrophenylthio)-1-(2-propynylamino)-2-nitroethylene, respectively, in the presence of about one equivalent of base, and there is produced in each case 1-nitro-2-(2-propynylamino)2-(2-mercaptoethyl)ethylene.

When the above product is reacted in a non-reactive solvent with 5-dimethylaminomethylfurfuryl chloride hydrochloride [prepared from thionyl chloride and 5-dimethylaminomethylfurfuryl alcohol, which itself is prepared according to the procedure described in *J. Chem. Soc.*, 4728 (1958)] and about two equivalents of base, there is produced 1-nitro-2-(2-propynylamino)-2-{2-[(5-dimethylaminomethyl-2-furyl)methylthio]ethylamino}ethylene (BL-5966).

Alternatively, the 1-nitro-2-(2-propynylamino)-2-(2-mercaptoethyl)ethylene may be reacted directly with 5-dimethylaminomethylfurfuryl alcohol in concentrated hydrochloric acid to produce 1-nitro-2-(2-propynylamino)-2-{2-[(5-dimethylaminomethyl-2-furyl)methylthio]ethylamino}ethylene (BL-5966).

EXAMPLE 12

N-Cyano-N'-(2-propyn-1-yl)-N''-{2-[(5-dimethylaminomethyl-2-furyl)methylthio]ethyl}guanidine (BL-5993)

A solution of N-cyano-N'-(2-propyn-1-yl)-N''-(2-mercaptoethyl)guanidine [prepared according to the procedure described in U.S. Pat. No. 4,112,234] in ethanol is reacted with an ethanol solution of about an equimolar amount of 5-dimethylaminomethylfurfuryl chloride hydrochloride and about two equivalents of base, and the title product is thereby produced.

EXAMPLE 13

The general procedure of Example 1 is repeated except that the 2-[(5-dimethylaminomethyl-2-furyl)methylthio]ethylamine utilized therein is replaced by an equimolar amount of 2-[(5-diethylaminomethyl-2-furyl)methylthio]ethylamine,
2-[(5-{[N-ethyl-N-methylamino]methyl}-2-furyl)methylthio]ethylamine,
2-[(5-{2-[dimethylamino]ethyl}-2-furyl)methylthio]ethylamine,
2-[(5-{3-[dimethylamino]propyl}-2-furyl)methylthio]ethylamine,
2-[(5-aminomethyl-2-furyl)methylthio]ethylamine and
2-[(5-{[1-pyrrolidinyl]methyl}-2-furyl)methylthio]ethylamine, respectively,

[each prepared by the procedure described in Belgian Patent No. 857,388], and there is thereby produced 1-nitro-2-(2-propynylamino)-2-{2-[(5-diethylaminomethyl-2-furyl)methylthio]ethylamino}ethylene,
1-nitro-2-(2-propynylamino)-2-{2-[(5-{[N-ethyl-N-methylamino]methyl}-2-furyl)methylthio]ethylamino}ethylene,
1-nitro-2-(2-propynylamino)-2-{2-[(5-{2-[dimethylamino]ethyl}-2-furyl)methylthio]ethylamino}ethylene,
1-nitro-2-(2-propynylamino)-2-{2-[(5-{3-[dimethylamino]propyl}-2-furyl)methylthio]ethylamino}ethylene,
1-nitro-2-(2-propynylamino)-2-{2-[(5-aminomethyl-2-furyl)methylthio]ethylamino}ethylene and
1-nitro-2-(2-propynylamino)-2-{2-[(5-[(1-pyrrolidinyl)methyl]-2-furyl)methylthio]ethylamino}ethylene, respectively.

EXAMPLE 14

1-Nitro-2-(2-propynylamino)-2-{2-[(5-{[N-methyl-N-propargylamino]methyl}-2-furyl)methylthio]ethylamino}ethylene The reaction of furfuryl alcohol and N-methylpropargylamine hydrochloride with paraformaldehyde according to the general procedure of *J. Chem. Soc.*, 4728 (1958), and treatment of the product with cysteamine hydrochloride followed by neutralization, produces 2-{(5-{[N-methyl-N-propargylamino]methyl}-2-furyl)methylthio}ethylamine. When the latter product is reacted with 1,1-bis(methylthio)-2-nitroethylene and then with propargylamine according to the general procedure of Example 1, the title compound is produced.

EXAMPLE 15

The general procedure of Example 14 is repeated, except that the N-methylpropargylamine hydrochloride is replaced by an equimolar amount of N-methylallylamine hydrochloride,
dipropargylamine hydrochloride,
allylamine hydrochloride,
N-methylaniline hydrochloride and
benzylamine hydrochloride, respectively,
and there is thereby produced 1-nitro-2-(2-propynylamino)-2-{2-[(5-{[N-methyl-N-allylamino]methyl}-2-furyl)methylthio]ethylamino}ethylene,
1-nitro-2-(2-propynylamino)-2-{2-[(5-dipropargylaminomethyl-2-furyl)methylthio]ethylamino}ethylene,
1-nitro-2-(2-propynylamino)-2-{2-[(5-allylaminomethyl-2-furyl)methylthio]ethylamino}ethylene,
1-Nitro-2-(2-propynylamino)-2-{2-[(5-{[N-methyl-N-phenylamino]methyl}-2-furyl)methylthio]ethylamino}ethylene and
1-nitro-2-(2-propynylamino)-2-{2-[(5-benzylaminomethyl-2-furyl)methylthio]ethylamino}ethylene, respectively.

EXAMPLE 16

N-Cyano-N'-(2-propyn-1-yl)-N''-{2-[(5-{[N-ethyl-N-methylamino]methyl}-2-furyl)methylthio]ethyl}guanidine When an isopropyl alcohol solution of dimethyl cyanodithioimidocarbonate [prepared according to the procedure described in *J. Org. Chem.*, 32, 1566 (1967)] is reacted with 2-[(5-{[N-ethyl-N-methylamino]methyl}-2-furyl)methylthio]ethylamine and the resultant N-cyano-N'-2-[(5-{[N-ethyl-N-methylamino]methyl}-2-furyl)methylthio]-ethyl}-S-methylisothiourea treated with propargylamine in the procedure of Example 2, there is produced N-cyano-N'-(2-propyn-1-yl)-N''-{2-[(5-{[N-ethyl-N-methylamino]methyl}-2-furyl)methylthio]ethyl}guanidine.

EXAMPLE 17

The general procedure of Example 16 is repeated except that the 2-[(5-{[N-ethyl-N-methylamino]methyl}-2-furyl)methylthio]ethylamine utilized therein is replaced by an equimolar amount of 2-[(5-diethylaminomethyl-2-furyl)methylthio]ethylamine,
2-[(5-{2-[dimethylamino]ethyl}-2-furyl)methylthio]ethylamine,
2-[(5-{3-[dimethylamino]propyl}-2-furyl)methylthio]ethylamine,
2-[(5-aminomethyl-2-furyl)methylthio]ethylamine,
2-[(5-{[1-pyrrolidinyl]methyl}-2-furyl)methylthio]ethylamine,
2-[(5-{[N-methyl-N-propargylamino]methyl}-2-furyl)methylthio]ethylamine,
2-[(5-{[N-methyl-N-allylamino]methyl}-2-furyl)methylthio]ethylamine,
2-[(5-dipropargylaminomethyl-2-furyl)methylthio]ethylamine,
2-[(5-allylaminomethyl-2-furyl)methylthio]ethylamine,
2-[(5-{[N-methyl-N-phenylamino]methyl}-2-furyl)methylthio]ethylamine and
2-[(5-benzylaminomethyl-2-furyl)methylthio]ethylamine, respectively,
and there is thereby produced N-cyano-N'-(2-propyn-1-yl)-N''-{2-[(5-diethylaminomethyl-2-furyl)methylthio]ethyl}guanidine,
N-cyano-N'-(2-propyn-1-yl)-N''-{2-[(5-{2-[dimethylamino]ethyl}-2-furyl)methylthio]ethyl}guanidine,
N-cyano-N'-(2-propyn-1-yl)-N''-{2-[(5-{3-[dimethylamino]propyl}-2-furyl)methylthio]ethyl}guanidine,
N-cyano-N'-(2-propyn-1-yl)-N''-{2-[(5-aminomethyl-2-furyl)methylthio]ethyl}guanidine,
N-cyano-N'-(2-propyn-1-yl)-N''-{2-[(5-{[1-pyrrolidinyl]methyl}-2-furyl)methylthio]ethyl}-guanidine,
N-cyano-N'-(2-propyn-1-yl)-N''-{2-[(5-{[N-methyl-N-propargylamino]methyl}-2-furyl)methylthio]ethyl}-guanidine,
N-cyano-N'-(2-propyn-1-yl)-N''-{2-[(5-{[N-methyl-N-allylamino]methyl}-2-furyl)methylthio]ethyl}guanidine,
N-cyano-N'-(2-propyn-1-yl)-N''-{2-[(5-dipropargylaminomethyl-2-furyl)methylthio]ethyl}guanidine,
N-cyano-N'-(2-propyn-1-yl)-N''-{2-[(5-allylaminomethyl-2-furyl)methylthio]ethyl}guanidine,
N-cyano-N'-(2-propyn-1-yl)-N''-{2-[(5-{[N-methyl-N-phenylamino]methyl}-2-furyl)methylthio]ethyl}-guanidine and
N-cyano-N'-(2-propyn-1-yl)-N''-{2-[(5-benzylaminomethyl-2-furyl)methylthio]ethyl}guanidine, respectively

EXAMPLE 18

1-Nitro-2-(2-propynylamino)-2-{2-[2-(5-dimethylaminomethyl-2-furyl)ethylthio]ethylamino}ethylene.

When 1-phthalimido-2-[2-(5-dimethylaminomethyl-2-furyl)ethylthio]ethane [prepared according to the procedure described in Belgian Pat. No. 857,388] is treated with hydrazine, and the resulting substituted ethylamine is reacted according to the general procedure of Example 1, the title product is produced.

EXAMPLE 19

1-Nitro-2-(2-propynylamino)-2-{3-[(5-dimethylaminomethyl-2-furyl)methylthio]-propylamino}ethylene When 1-phthalimido-3-[(5-dimethylaminomethyl-2-furyl)methylthio]propane [prepared according to the procedure described in Belgian Pat. No. 857,388] is treated with hydrazine, and the resulting substituted propylamine is reacted according to the general procedure of Example 1, the title product is produced.

EXAMPLE 20

N-Cyano-N'-(2-propyn-1-yl)-N''-{2-[2-(5-dimethylaminomethyl-2-furyl)ethylthio]ethyl}guanidine When 1-phthalimido-2-[2-(5-dimethylaminomethyl-2-furyl)ethylthio]ethane is treated with hydrazine and the resultant substituted ethylamine is reacted with dimethyl cyanodithioimidocarbonate there is produced N-cyano-N'-{2-[2-(5-dimethylaminomethyl-2-furyl)ethylthio]ethyl}-S-methylisothiourea, and when this is reacted with propargylamine according to the general procedure of Example 3 the title compound is produced.

EXAMPLE 21

N-Cyano-N'-(2-propyn-1-yl)-N''-{3-[(5-dimethylaminomethyl-2-furyl)methylthio]propyl}guanidine When 1-phthalimido-3-[(5-dimethylaminomethyl-2-furyl)methylthio]propane is treated with hydrazine and the resultant substituted propylamine is reacted with dimethyl cyanodithioimidocarbonate there is produced N-cyano-N'-{3-[(5-dimethylaminomethyl-2-furyl)methylthio]propyl}-S-methylisothiourea, and when this is reacted with propargylamine according to the general procedure of Example 3 the title compound is produced.

EXAMPLE 22

1-Phenylsulfonyl-2-(2-propynylamino)-2-{2-[(5-dimethylaminomethyl-2-furyl)methylthio]ethylamino}ethylene Reaction of methyl phenyl sulfone with carbon disulfide under strongly basic conditions and treatment with methyl iodide yields 1-phenylsulfonyl-2,2-bis(methylthio)ethylene, a known compound which is described in *Bull. Soc. Chim. Fr.*, 673 (1973). When the latter compound is reacted with 2-[(5-dimethylaminomethyl-2-furyl)methylthio]ethylamine according to the general procedure of Example 1, the title product is produced.

EXAMPLE 23

The general procedure of Example 22 is repeated except that the methyl phenyl sulfone utilized therein is replaced by an equimolar amount of 4-chlorophenyl methyl sulfone,
3,4-dichlorophenyl methyl sulfone,
4-methylphenyl methyl sulfone and
dimethyl sulfone, respectively,

[each prepared by the general procedure described in *Bull. Soc. Chim. Fr.*, 637 (1973)] and there is thereby produced 1-(4-chlorophenylsulfonyl)-2-(2-propynylamino)-2-{2-[(5-dimethylaminomethyl-2-furyl)methylthio]ethylamino}ethylene,
1-(3,4-dichlorophenylsulfonyl)-2-(2-propynylamino)-2-{2-[(5-dimethylaminomethyl-2-furyl)methylthio]ethylamino}ethylene,
1-(4-methylphenylsulfonyl)-2-(2-propynylamino)-2-{2-[(5-dimethylaminomethyl-2-furyl)methylthio]ethylamino}ethylene and
1-(methylsulfonyl)-2-(2-propynylamino)-2-{2-[(5-dimethylaminomethyl-2-furyl)methylthio]ethylamino}ethylene, respectively.

EXAMPLE 24

1-Cyano-2-(2-propynylamino)-2-{2-[(5-dimethylaminomethyl-2-furyl)methylthio]ethylamino}ethylene When 2-[(5-dimethylaminomethyl-2-furyl)methylthio]ethylamine is reacted with 1-cyano-2-ethoxy-2-propynylaminoethylene [prepared from propargylamine and 1-cyano-2,2-bis(ethoxy)ethylene, which itself is prepared by the procedure described in *J. Am. Chem. Soc.*, 71, 47 (1949)], the title product is produced.

Alternatively, when 2-[(5-dimethylaminomethyl-2-furyl)methylthio]ethylamine is reacted with 1-cyano-2,2-bis(methoxy)ethylene and the resultant 1-cyano-2-methoxy-2-{2-[(5-dimethylaminomethyl-2-furyl)methylthio]ethylamino}ethylene is reacted with propargylamine according to the general procedure of Example 1, the title product is produced.

EXAMPLE 25

1-Nitro-2-(2-propynylamino)-2-{2-[(3-methyl-5-dimethylaminomethyl-2-furyl)methylthio]ethylamino}ethylene A. 2-[(3-Methyl-5-dimethylaminomethyl-2-furyl)methylthio]ethylamine The reaction of 3-methyl-2-furfuryl alcohol [prepared according to the procedure described in *J. Am. Chem. Soc.*, 72, 2195 (1950)] and dimethylamine hydrochloride with paraformaldehyde according to the general procedure described in *J. Chem. Soc.*, 4728 (1958), and treatment of the resultant product with cysteamine hydrochloride, followed by neutralization, produces the title product.

B.
1-Nitro-2-(2-propynylamino)-2-{2-[(3-methyl-5-dimethylaminomethyl-2-furyl)methylthio]ethylamino}ethylene When the product of Step A is reacted according to the procedure of Example 1, Steps A and B, the title product is produced.

EXAMPLE 26

The general procedure of Example 25 is repeated except that the dimethylamine hydrochloride utilized therein is replaced by an equimolar amount of methylamine hydrochloride,
ethylmethylamine hydrochloride,
N-methylpropargylamine hydrochloride and
diethylamine hydrochloride, respectively, and there is thereby produced 1-nitro-2-(2-propynylamino)-2-{2-[(3-methyl-5-methylaminomethyl-2-furyl)methylthio]ethylamino}ethylene,
1-nitro-2-(2-propynylamino)-2-{2-[(3-methyl-5-[N-ethyl-N-methylamino]methyl-2-furyl)methylthio]ethylamino}ethylene,
1-nitro-2-(2-propynylamino)-2-{2-[(3-methyl-5-[N-methyl-N-propargylamino]methyl-2-furyl)methylthio]ethylamino}ethylene and
1-nitro-2-(2-propynylamino)-2-{2-[(3-methyl-5-diethylaminomethyl-2-furyl)methylthio]ethylamino}ethylene, respectively.

EXAMPLE 27

N-Cyano-N'-(2-propyn-1-yl)-N''-{2-[(3-methyl-5-dimethylaminomethyl-2-furyl)methylthio]ethyl}guanidine When an alcohol solution of dimethyl cyanodithioimidocarbonate is reacted with 2-[(3-methyl-5-dimethylaminomethyl-2-furyl)methylthio]ethylamine, and the resultant N-cyano-N'-{2-[(3-methyl-5-dimethylaminomethyl-2-furyl)methylthio]ethyl}-S-methylisothiourea is treated with propargylamine according to the general procedure of Example 3, the title compound is produced.

EXAMPLE 28

The general procedure of Example 27 is repeated except that the 2-[(3-methyl-5-dimethylaminomethyl-2-furyl)methylthio]ethylamine utilized therein is replaced by an equimolar amount of 2-[(3-methyl-5-methylaminomethyl-2-furyl)methylthio]ethylamine, 2-{(3-methyl-5-[N-ethyl-N-methylamino]methyl-2-furyl)methylthio}ethylamine, 2-{(3-methyl-5-[N-methyl-N-propargylamino]methyl-2-furyl)methylthio}ethylamine and 2-[(3-methyl-5-diethylaminomethyl-2-furyl)methylthio]ethylamine, respectively, and there is thereby produced N-cyano-N'-(2-propyn-1-yl)-N''-{2-[(3-methyl-5-methylaminomethyl-2-furyl)methylthio]ethyl}guanidine, N-cyano-N'-(2-propyn-1-yl)-N''-{2-[(3-methyl-5-[N-ethyl-N-methylamino]methyl-2-furyl)methylthio]ethyl}guanidine, N-cyano-N'-(2-propyn-1-yl)-N''-{2-[(3-methyl-5-[N-methyl-N-propargylamino]methyl-2-furyl)methylthio]ethyl}guanidine and N-cyano-N'-(2-propyn-1-yl)-N''-{2-[(3-methyl-5-diethylaminomethyl-2-furyl)methylthio]ethyl}guanidine, respectively.

EXAMPLE 29

N-Phenylsulfonyl-N'-(2-propyn-1-yl)-N''-{2-[(5-dimethylaminomethyl-2-furyl)methylthio]ethyl}guanidine Reaction of N-phenylsulfonylimidodithiocarbonic acid dimethyl ester [prepared by the general procedure described in Chem. Ber., 99, 2885 (1966)] with 2-[(5-dimethylaminomethyl-2-furyl)methylthio]ethylamine and reaction of the resultant product with excess propargylamine according to the general procedure of Example 3 yields the title product.

EXAMPLE 30

The general procedure of Example 29 is repeated except that the N-phenylsulfonylimidodithiocarbonic acid dimethyl ester is replaced by an equimolar amount of N-(4-chlorophenylsulfonyl)imidodithiocarbonic acid dimethyl ester, N-(4-methylphenylsulfonyl)imidodithiocarbonic acid dimethyl ester and N-methylsulfonylimidodithiocarbonic acid dimethyl ester, respectively, and there is thereby produced N-(4-chlorophenylsulfonyl)-N'-(2-propyn-1-yl)-N''-{2-[(5-dimethylaminomethyl-2-furyl)methylthio]ethyl}guanidine, N-(4-methylphenylsulfonyl)-N'-(2-propyn-1-yl)-N''-{2-[(5-dimethylaminomethyl-2-furyl)methylthio]ethyl}guanidine and N-methylsulfonyl-N'-(2-propyn-1-yl)-N''-{2-[(5-dimethylaminomethyl-2-furyl)methylthio]ethyl}guanidine, respectively.

We claim:

1. A compound of the formula

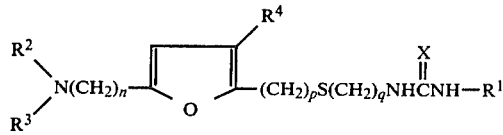

wherein $R^1$ is a straight or branched chain alkynyl group containing from 3 to 9 carbon atoms, inclusive; $R^2$ and $R^3$ are the same or different and are hydrogen, (lower)alkyl, (lower)alkenyl, (lower)alkynyl or Ar; $R^4$ is hydrogen or (lower)alkyl; n is an integer of from 1 to 6; p is 1 or 2 and q is 2 or 3, provided that the sum of p and q is 3 or 4; X is $NR^5$ or $CHR^5$; $R^5$ is cyano, nitro, $SO_2Ar$ or $SO_2$(lower)alkyl; and Ar is phenyl or phenyl containing one or two substituents independently selected from (lower)alkyl and halogen, or a nontoxic, pharmaceutically acceptable salt thereof.

2. A compound of claim 1 having the formula

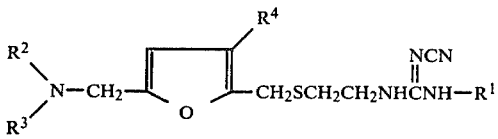

wherein $R^1$, $R^2$, $R^3$ and $R^4$ are as defined in claim 1, or a nontoxic, pharmaceutically acceptable salt thereof.

3. A compound of claim 1 having the formula

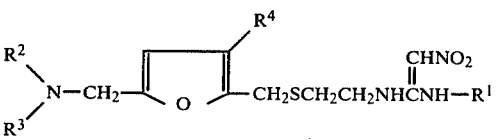

wherein $R^1$, $R^2$, $R^3$ and $R^4$ are as defined in claim 1, or a nontoxic, pharmaceutically acceptable salt thereof.

4. A compound of the formula

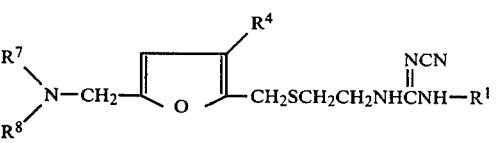

wherein $R^1$ is a straight or branched chain alkynyl group containing from 3 to 9 carbon atoms, inclusive; $R^4$ is hydrogen or (lower)alkyl; and $R^7$ and $R^8$ are the same or different and are hydrogen or (lower)alkyl; or a nontoxic, pharmaceutically acceptable salt thereof.

5. A compound of the formula

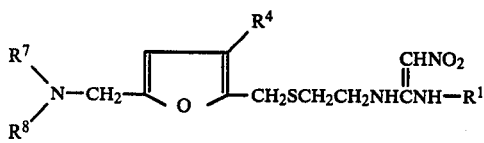

wherein R[1] is a straight or branched chain alkynyl group containing from 3 to 9 carbon atoms, inclusive; R[4] is hydrogen or (lower)alkyl; and R[7] and R[8] are the same or different and are hydrogen or (lower)alkyl; or a nontoxic, pharmaceutically acceptable salt thereof.

6. A compound of claim 4 having the formula

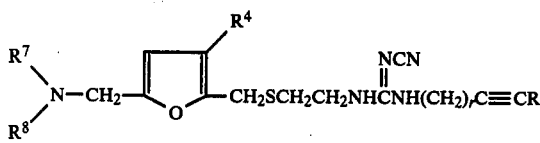

wherein R[4], R[7] and R[8] are as defined in claim 4, r is an integer of from 1 to 6, inclusive, and R[9] is hydrogen or methyl, or a nontoxic, pharmaceutically acceptable salt thereof.

7. A compound of claim 5 having the formula

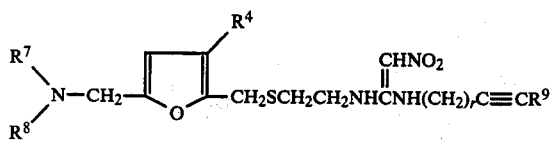

wherein R[4], R[7] and R[8] are as defined in claim 5, r is an integer of from 1 to 6, inclusive, and R[9] is hydrogen or methyl, or a nontoxic, pharmaceutically acceptable salt thereof.

8. A compound of claim 4 having the formula

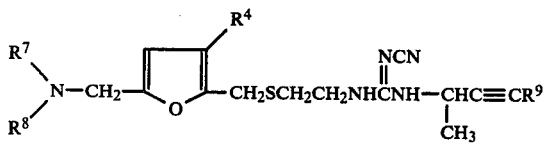

wherein R[4], R[7] and R[8] are as defined in claim 4 and R[9] is hydrogen or methyl, or a nontoxic, pharmaceutically acceptable salt thereof.

9. A compound of claim 5 having the formula

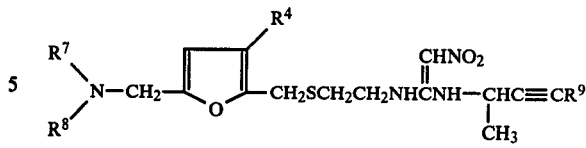

wherein R[4], R[7] and R[8] are as defined in claim 5 and R[9] is hydrogen or methyl, or a nontoxic, pharmaceutically acceptable salt thereof.

10. A compound of claim 4 having the formula

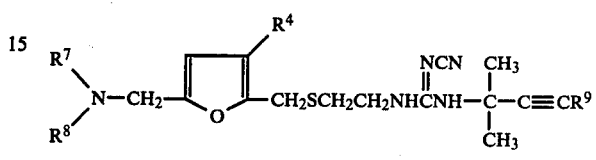

wherein R[4], R[7] and R[8] are as defined in claim 4 and R[9] is hydrogen or methyl, or a nontoxic, pharmaceutically acceptable salt thereof.

11. A compound of claim 5 having the formula

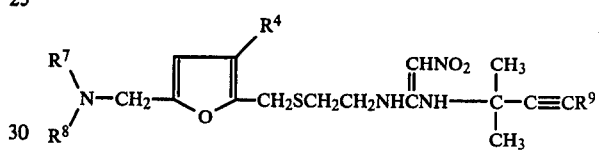

wherein R[4], R[7] and R[8] are as defined in claim 5 and R[9] is hydrogen or methyl, or a nontoxic, pharmaceutically acceptable salt thereof.

12. The compound of the formula

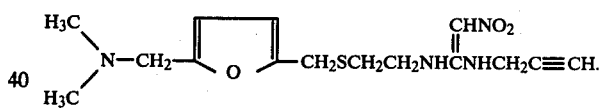

13. A nontoxic, pharmaceutically acceptable salt of the compound of claim 12.

14. The compound of the formula

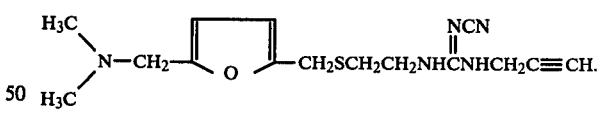

15. A nontoxic, pharmaceutically acceptable salt of the compound of claim 14.

* * * * *

UNITED STATES PATENT AND TRADEMARK OFFICE
CERTIFICATE OF CORRECTION

PATENT NO. : 4,203,909
DATED : May 20, 1980
INVENTOR(S) : Aldo A. Algieri and Ronnie R. Crenshaw It is certified that error appears in the above-identified patent and that said Letters Patent are hereby corrected as shown below:

In Column 2, Line 12, the correct structural formula should read

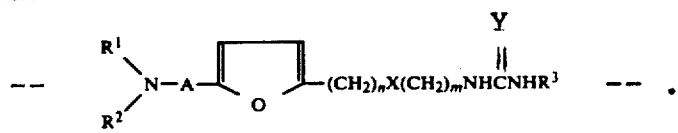

Signed and Sealed this

Twenty-ninth Day of July 1980

[SEAL]

Attest:

SIDNEY A. DIAMOND

Attesting Officer

Commissioner of Patents and Trademarks